(12) United States Patent
Van Der Zee

(10) Patent No.: US 6,465,517 B1
(45) Date of Patent: Oct. 15, 2002

(54) COMPOSITION FOR THE TREATMENT OF MIGRAINE

(75) Inventor: Luutsche Van Der Zee, Arnhem (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 09/613,573

(22) Filed: Jul. 11, 2000

(51) Int. Cl.[7] .................... A61K 31/185; A61K 31/194; A61K 31/195; A61K 31/122; A61K 31/355; A61K 31/375; A61K 33/04; A61K 33/06; A61K 35/78

(52) U.S. Cl. .................... 514/562; 514/251; 514/276; 514/458; 514/474; 514/547; 514/556; 514/561; 514/565; 514/578; 514/665; 514/690; 514/706; 514/904; 514/905; 424/670; 424/679; 424/681; 424/682; 424/683; 424/686; 424/688; 424/692; 424/697; 424/702; 424/722; 424/756; 424/764; 426/72; 426/74

(58) Field of Search .................... 426/72, 74; 514/904, 514/905, 251, 276, 458, 474, 547, 556, 561, 565, 578, 690, 706, 665, 562; 424/670, 679, 681–683, 686, 688, 692, 697, 702, 722, 725, 756

(56) References Cited

U.S. PATENT DOCUMENTS 6,068,999 A 5/2000 Hendrix 6,232,346 B1 * 5/2001 Sole et al. .................... 514/561

FOREIGN PATENT DOCUMENTS

| DE | 199 05 879 A1 | 8/2000 |
| DE | 199 07 586 A1 | 8/2000 |
| EP | 0 288 447 A1 | 10/1988 |
| WO | WO 98/43617 | 10/1998 |

OTHER PUBLICATIONS

Chemical Abstracts, document No. 135:101819 (2001).*
"WPI World Patent Information Derwent, Derwent, GB", vol. 8, NR. 96 XP002079121: Abstract for JP7330584, applicant Taisho Pharm Co Ltd., Dec. 19, 1995, "Agent for Treating Fatigue . . . ".
Database WPI, Derwent Publications Ltd., XP002187988: Abstract for CN1107053, applicant Ruifulai Pharm Co Ltd, Aug. 23, 1995, "Medicine Cure Headache".

* cited by examiner

Primary Examiner—John Pak
(74) Attorney, Agent, or Firm—Browdy and Neimark, P.L.L.C.

(57) ABSTRACT

The present invention describes a novel composition for the treatment of migraine, a common neurovascular syndrome, which can be elicited by functional and/or structural (symptomatic) disorders. This composition comprises taurine, coenzyme Q10 and additionally creatine, L-carnitine, certain vitamins and minerals, carbohydrates, proteins, fats and herbal extracts. Furthermore, the invention describes a method for the treatment of migraine.

19 Claims, No Drawings

COMPOSITION FOR THE TREATMENT OF MIGRAINE

FIELD OF THE INVENTION

The present invention pertains to a nutritional composition and a method for the treatment of migraine.

BACKGROUND

Migraine is a neurological multifactorial syndrome, of which headache is only one of the many ways the disease manifests itself. Migraine is characterised by recurrent attacks of severe, pulsating and disabling headache, vomitting, photo- and phonofobia and malaise, which worsens with movement. In 20% of the patients additional transient focal neurological (aura) symptoms may occur. The exact mechanism is unknown, but generic factors might be involved in the disease. Patients may suffer from a defect in ion channels and have a disturbed energy metabolism in brain and skeletal muscle. These above described features are not observed with ordinary headache such as for example tension headache. The prevalence or migraine is 17.6% for women and 6% for men. The disease is characterised by attacks of severe headache and autonomic or neurological symptoms. The attacks occur in two forms, migraine without aura (common migraine), which occurs in 75% of the patients and with aura (classic migraine), occur in about 30% of the migraineurs. Both types however are experienced in one third of the subjects.

Enhanced central neuronal excitability and susceptibility to spontaneous neuronal depolarisation characterise migraine with aura and possibly without aura. The mechanism behind a migraine attack is still not completely unravelled, due to the diversity of the complaints and the lack of good animal models for migraine. However, there is increasing evidence that a wide range of mechanisms is involved in the pathogenesis of migraine, of which the phenomenon of spreading depression (SD) plays an obligate part. A wave of hyperexcitability spreads out and passes over the cortical surface at a rate of 2–3 mm per minute. In the wake of the wave of excitation, the previously hyperactive cortical neurons become depolarised and electrically quiescent—or depressed—for some minutes. The loss of proper ionic gradients across the membrane following hyperexcitation is associated with marked changes in ion levels of the cortical extracellular fluid, including a remarkable increase in extracellular potassium.

Electrical excitability of skeletal and cardiac muscle cells and neurons results from a balance of inhibitory and excitatory influences. A large number of voltage-gated ion channels, ligand-gated channels, transporters and ATP-dependent pumps are involved in maintaining this balance. Ionic concentration gradients across the membrane can be established and maintained because the lipid bilayer is an extremely good insulator. Establishment of the gradient is highly ATP-dependent and achieved by ATP-dependent pumps. Once the ionic gradient is achieved, movement of one or more ions down their respective concentration gradients results in signaling voltage differences across a membrane. Normal membrane excitability is tightly regulated by the balance of these opposing influences and dependent on cellular energy metabolism for the delivery of appropriate amounts of ATP. Mitochondrial dysfunctioning therefore may result in disruption of the delicate balance, by limiting proper functioning of the ATP-dependent pumps. This results in a change of the excitability of various cells. Large changes in excitability of muscle or nerve may well be lethal, but subtle changes in some ion channels can lead to a slight increase in membrane excitability that may result in seizures, epilepsy or migraine headache (Ptacek, L. J. (1999) Semin. Neurol. 19, 363–369). Usually these diseases are episodic, and nerve or muscle may function properly under many circumstances. However, during stress (or other ATP consuming circumstances for example) a precipitating event can lead to periodically abnormal excitability.

Different neurophysiological, cerebral blood flow (CBF) and brain metabolic measures confirm the hypothesis that a disturbed cellular energy metabolism is associated with and may lead to changes in neuronal excitability and susceptibility to spreading depression or activation in migraine. Positron Emission Tomography (PET) measurements in several centers have shown increased mitochondrial oxygen consumption in the brains of patients with migraine. Studies using $^{31}$P-MRS have provided evidence of mitochondrial abnormality in platelets and in muscle tissue and have shown a disordered cerebral energy metabolism in patients with migraine. Barbiroli, B., et a. (1992) Neurology 42, 1209–1214 studied brain and muscle energy metabolism by $^{31}$P MRS in 12 patients affected by migraine with aura (classic migraine) in distinct periods. Brain $^{31}$P-MRS disclosed a low phosphocreatine content in all patients, accompanied by high ADP concentrations, a high percentage of V/Vmax (ATP), and low phosphorylation potential-features showing an unstable state of metabolism in classic migraine. Abnormal muscle mitochondrial function, in the absence of clinical signs of muscle impairment, was present in nine of the 12 patients examined. In another study conducted with migraine patients, brain energy phosphate metabolism and intracellular pH (pHi) was studied in a cross-sectional study by in vivo $^{31}$P NMR spectroscopy as well. During a migraine attack the ratio ATP/total phosphate signal (mole % ATP) was preserved, but there was a decrease in mole % phosphocreatine (PCr) and an increase in mole % inorganic phosphate (Pi), resulting in a decrease of the PCr/Pi ratio, an index of brain phosphorylation potential. This was found in classic but not common migraine. Mole % Pi was also increased in combined brain regions between attacks. There was no alteration in brain pHi during or between attacks. Energy phosphate metabolism but not pHi appears disordered during a migraine attack in this study (Welch, K. M., et al. (1989) Neurology 39, 538–541). Lodi et al. (1997) J. Neurol. Sci. 146, 73–80 also used $^{31}$P-MRS to quantify skeletal muscle bioenergetics and proton efflux in 63 patients with migraine (23 with migraine without aura, MwoA, 22 with migraine with aura, MwA, and 18 with prolonged aura or stroke, CM) and in 14 patients with cluster headache (CH), all in an attack-free period. At rest, mitochondrial function was abnormal only in CM, as shown by a low phosphocreatine (PCr) concentration. At the end of a mixed glycolytic/aerobic exercise all three migraine groups showed a significantly smaller decrease of cytosolic pH compared to controls with a similar end-exercise PCr breakdown, while end-exercise pH was normal in cluster headache patients. The normal rate of proton efflux in all headache groups suggests that the reduced end-exercise acidification was due to a reduction of glycolytic flux in migraine patients. The maximum rate of mitochondrial ATP production (Qmax), calculated from the rate of post-exercise PCr recovery and the end-exercise [ADP], was low in cluster headache patients as well as in migraine patients, except in MwoA patients. In conclusion, the study by Lodi et al. shows that the muscle mitochondrial failure, present in migraine as well as cluster headache patients, is in the former associated with a reduced glycolytic flux, while in the latter the glycolytic flux is normal.

The disturbed energy metabolism is not restricted to migraine type of headache. In a study by Montagna P. et al., (1997) Neurology 48, 113–119, $^{31}$P MRS on the brain and skeletal muscles of 14 patients affected with cluster headache (CH) was performed. Patients were examined in various periods and nine of them also during the cluster period, although not during the attack. Brain 31P MRS showed reduced phosphocreatine (PCr) levels, an in creased ADP concentration (calculated from the creatine kinase equilibrium), a reduced phosphorylation potential, and a high relative rate of ATP biosynthesis (% of V/Vmax). The inorganic phosphate (Pi) content was increased during the cluster period. Ten of 13 patients also showed a slow rate of PCr recovery in muscle after the exercise. $^{31}$P-MRS in CH patients showed abnormalities of brain and seletal muscle energy metabolism comparable with those seen in various types of migraine, thus suggesting a similarity in biochemical pathogenic mechanisms between CH and migraine.

Thus a disturbed mitochondrial ATP production may lead to changes in neuronal excitability, and susceptibility to spreading depression or activation in migraine. An effective approach for the treatment of migraine might therefore be the administration of components that improve the cellular energy metabolism.

At the moment such an approach does not exist. A number of different therapies are available to prevent or alleviate migraine, but complete avoidance of the disease seems to be impossible and most of the prescribed drugs are known for their undesired side-effects. Preventive efficacy of some β-adrenoreceptor antagonists (propranolol, metoprolol, atenolol) are described. However, the β-blockers have multiple side effects, like hypotension, tiredness, increased weight and breathlessness. For long time ergotamine or other ergot alkaloids were the only drug for the treatment of migraine. They are reported to induce a strong vasocontraction and thereby probably preventing the vasodilation and increased blood flow causing headaches. However, controlled trials are lacking or of little value, They have low oral and rectal bioavailablity and may cause nausea, muscle cramps, or peripheral vasoconstriction. The 5-HT derivatives or triptans are highly selective for 5-HT receptors (1B, 1D, 1F), inhibiting vasodilatation, attenuating excitation and inducing vasoconstriction. Side effects usually consist of dizziness, heaviness or pressure on the chest and arms, shortness of breath, and sometimes chest pain. Triptans are contra-indicated for patients with coronary artery disease. Further, calcium channel blockers, hormonal manipulators and non-steroidal anti-inflammatory drugs (NSAID's) are sometimes prescribed, but evidence for preventive efficacy is rare.

U.S. Pat. No. 4,962,121 (Hamberger and Van Gelder) discloses a method and a composition for the treatment of migraine by influencing the nerve cells. The compositions to be used in such treatment include taurine, L-carnitine, zinc and calcium. Other amino acids to be administered are glycine, leucine, histidine and proline WO 97/26897 describes the use of a combination of potassium, magnesium and pyridoxin (vitamin B6) together with nutrients and common analgesics for the treatment of migraine.

WO 98/43617 discloses nutritional compositions for improving deficiencies in mitochondrial energy production, such as occurring in cardiac failure. The compositions contain L-carnitine (at least 3 g/day), coenzyme Q10 (at least 150 mg/day) and taurine (at least 3 g/day), and may further contain creatine, cysteine, vitamins C and E, thiamin and selenium.

SUMMARY OF THE INVENTION

A novel composition for the treatment of migraine has now been found. The composition of the invention comprises taurine and coenzyme Q10. The composition may further contain one or more components selected from creatine, L-carnitine, vitamin C and E, selenium and one or more of the components thiamine, riboflavin, magnesium or potassium. Additionally, the invention pertains to a composition comprising carbohydrates, proteins, fats and herbal extracts. The invention furthermore pertains to a method for the treatment of migraine comprising administering such compositions.

DESCRIPTION OF THE INVENTION

Adequate energy production by proper mitochondrial functioning is very important for the functioning and survival of every cell, particularly for highly active cells like myocytes and brain cells. Energy (ATP) production from the nutrients out of our food, is a well co-ordinated but very complicated process and needs the presence of a number of co-factors. Insufficient levels of factors like CoQ10 (antioxidant and key transducer for mitochondrial oxidative phosphorylation), taurine (important for calcium homeostasis), creatine (important as a high energy phosphate (P) shuttle and energy reservoir) and L-carnitine (regulating glycolysis and essential for transport of fatty acids across the mitochondrial membrane) reduce the energy producing capacity and therefore vitality of the cell.

Normalisation of only one factor is usually not sufficient to improve the energy production in the presence of abnormalities in more than one actor in the bioenergetic pathway. This pathway consists of a cascade of interlocking activities in which the nutrients and co-factors are highly dependent on each other and act synergistically. Therefore, the combination of the above mentioned components will interact to benefit the patient and the effect of the combination is expected to be greater than the sum of the effect of the individual ingredients alone. The invention pertains to a composition which provides a balanced combination of components enhancing the cellular energy status of neurons and other brain cells and facilitating maintenance of ion gradients, and thus providing alleviation of migraine. The composition of the invention contains one or more of the components CoQ10, L-carnitine, taurine and creatine (B-vitamins), of which taurine and CoQ10 are believed to be the most important ones. As mentioned before, the combination of the individual components addresses a cascading series of disruptions in cellular energetics that are present in patients with migraine and will therefore be more effective than treatment with a single component alone. Moreover, the composition of the invention is found to be safe and no side-effects have been reported for healthy volunteers in a recently performed clinical trial.

Taurine

Taurine (2-aminoethanesulfonic acid) is the amino acid with the highest concentration in the human body. Its physiologic functions are not yet well understood. Taurine is considered to be important for the maintenance of the intracellular ion, in particular calcium, homeostasis. Taurine appears to do this by affecting several membrane systems. It modulates calcium and sodium channels through the cellular calcium/sodium-exchanger and a taurine/sodium-exchanger (Azuma, Satoh). Furthermore, taurine can act as an antioxidant and may react with a variety of potentially toxic intracellular aldehydes, including malonic dialdehyde (Ogasawara). Therefore, increased levels of cerebral taurine may dampen the hyperexcitation required to initiate SD by preventing derangements in ion gradients across the membrane and preventing calcium overload in the mitochondria, leading to malfunctioning of the mitochondria and cellular apoptosis.

Furthermore, taurine displays inhibitory neurotransmitter properties over sensitive pathways in the brain stem and spinal cord. It might therefore be possible that an increase of central and peripheral levels of taurine during painful events could represent a reactive defensive mechanism. Although there are few reports regarding taurine's action on SD, it is notable that taurine has anti-epileptic properties in many animal models. Patients with migraine have significantly higher taurine levels in plasma and cerebrospinal fluid than controls. No sex or age influence over the amino acid levels were observed. Plasma taurine levels in patients with classic migraine correlated negatively with severity of headache. Central taurine liberation during migraine crisis may be due to spontaneous depolarisation or a defensive reaction in the context of cerebral homeostatic processes. It is therefore important to prevent taurine depletion and guarantee optimal taurine supplementation in these patients. Instead of taurine itself taurates may be used in the composition of the invention.

CoQ10

CoQ10 (coenzyme Q10, ubiquinone 50, 2,3-dimethoxy-5-methyl6-pentacontdacaenyl-benzoquinone) plays a vital role as a rate-limiting carrier for the flow of electrons through the mitochondrial complexes I, II and II of the respiratory chain, hereby maintaining or improving energy (ATP) generation by the mitochondria. It is also a major lipophilic antioxidant. The molecule is located in the inner mitochondrial membrane but is also associated wit the membrane of other intracellular organelles. CoQ10 thus maintains redox activity and electron flow across different membranes (Villalba, Crane) and guaranteeing optimal mitochondrial functioning. In diseases like heart failure, mitochondrial dysfunction plays an important role in the reduced cardiac muscle contractility. Reduced levels (up to 50%) of CoQ10 in cardiac and skeletal muscle of patients with heart failure has been found (Folkers). Oral treatnent with CoQ10 has been shown to have beneficial effects on the course of cardiovascular disease in a wide variety of animal models. A meta-analysis of 8 controlled clinical trials (to 1997) revealed a significant improvement of several important cardiac parameters as ejection fraction, stroke volume, cardiac output and end-diastolic volume index by improving cellular energy metabolism (Soja).

The components indicated can be partly or wholly substituted by their functional equivalents. For example taurates can be used for taurine, and ubiquinones having isoprenoid side chains of 6–10 isoprenyl units can replace CoQ10; likewise L-carnitine equivalents include its base or salts such as the hydrochloride, as awell as its acylated forms, such as acetyl, propionyl, butyryl, succinyl L-carnitine and esters and the like or any L-carnitine that is able to transfer the blood-brain barrier, in particular lipophilic forms of L-carnitine, and creatine equivalents include the anhydrous or hydrated base or salts such as crystalline hemisulfate. The amounts of components to be used in the compositions are as indicated in the appending claims. In addition to taurine, CoQ10 and optionally creatine and carnitine, further components are preferably present such as ascorbic acid (vitamin C), tocopherols (vitamin E), selenium, thiamine, riboflavin, magnesium and potassium, either individually or in any combination.

In a preferred embodiment of the invention extracts of feverfew (Chrysanthemum parthenium) and/or ginger (Zingiber officinale) are incorporated in the compositions. Preferably, the feverfew extracts contain more than 0.4% parthenolides. Such a high percentage is obtained when the feverfew extracts are made of feverfew leaves. The compositions may contain at least 50 mg, preferably at least 100 mg and more preferably 150 mg up to about 500 mg of the above mentioned feverfew extract per (daily) serving. Other sources of parthenolides may also be used. Preferably, the ginger extracts contain more man 4% gingerols. Such a high percentage is obtained when the ginger extracts are made of ginger roots. The compositions preferably contain at least 50 mg, preferably at least 100 mg and more preferably about 150 mg, up to about 500 mg of the above mentioned ginger extract per serving.

The compositions can be pharmaceutical compositions, containing the active ingredients as such, together with suitable excipients, or they can be nutritional compositions containing the active ingredients together with one or more food components. These food components may include carbohydrates, in particular malto-dextrins, fats and/or proteins, and optionally further components such as vitamins, minerals, etc. The nutritional compositions can be complete foods containing e.g. 100–250 g carbohydrates, 75–225 g proteins and 25–75 g fats, or, preferably, food supplements, containing e.g. 10–100 g carbohydrates, 0–75 g proteins and 0–25 g fats, all on a daily basis. The product can be a liquid or a powder which can be reconstituted to a liquid or can be added to other food components. In case of a liquid or a reconstitutable liquid, the amount of ingredients given on a daily basis can be incorporated in a volume of e.g. 0.5 liter, 1 liter, or 1.5 liter or another unit volume. The product can also be a tablet, pill, capsule, sachet, syrup, liquid or the like, not containing further food components, wherein the daily amounts are incorporated in a single daily dosage unit, or divided over 2, 3 or more daily dosage units. The compositions of WO 98/43617 may also be used in the present invention.

The compositions can be administered curatively or, especially, preventively for a prolonged period of time to patients suffering from repeated of chronic migraine or to persons who are predisposed to migraine. The compositions may also be used to support medication in case of acute migraines.

Table 1 below shows general and preferred ranges for the major components according to the invention.

TABLE 1

Ranges per daily dose.

| components | broadest range | preferred range | most preferred range |
|---|---|---|---|
| taurine | 0.1–10 g | 0.8–6 g | 1.2–4 g |
| CoQ10 | 8–800 mg | 15–300 mg | 50–200 mg |
| L-carnitine | 0.01–10 g | 0.5–8 g | 1.6 g |
| creatine | 0.5–20 g | 1–15 g | 1.5–10 g |
| vitamin C | 20 mg–2 g | 50 mg–1 g | 100–500 mg |
| vitamin E | 100–1500 IU | 150–1000 IU | 180–700 IU |
| thiamine | 1–100 mg | 1.5–30 mg | 2.5–20 mg |
| magnesium | 5–500 mg | | |

EXAMPLES

Example 1

A Powder Packed in a Can Consisting Per 100 g of:

28 g taurine 1.5 g coenzyme Q10

22 g acetyl-L-carnitine 28 g creatine 2.5 g vitamin C

5400 IU vitamin E 2 mg sodium selenite 250 mg thiamine 500 mg magnesium carbonate Make up to 100 g with maltodextrin DH 19.

10 g of the powder is dissolved in a glass of juice or milk shortly before consumption.

Example 2

Powder Packed in a Sachet of 10 g Consisting of:

2 g taurine 0.1 g coenzyme Q10

2.0 g L-carnitine.HCl 3 g creatine sulfate 10 mg thiamine.HCl 400 mg magnesium chloride 20 mg zinc carbonate Example 3

Tablet Comprising:

150 mg feverfew leaves extract 150 mg ginger root 300 mg magnesium oxide 250 mg taurine 50 mg coenzyme Q10

Two tablets should be taken per day.

What is claimed is:

1. A method for the treatment of migraine, comprising administering to a patient in need thereof 0.1–10 g taurine and 8–800 mg CoQ10 per day.

2. The method of claim 1, further comprising administering 0.5–20 g creatine and/or 0.01–10 g L-carnitine or acylated carnitine per day.

3. The method of claim 1 further comprising administering, on a daily dosage basis, one or more members selected from the group consisting of 50–500 mg feverfew extract, 50–500 mg ginger extract, 20 mg–2 g vitamin C, 100–1500 IU vitamin E, 15–200 µg selenium, 1–100 mg thiamine, 1–10 mg riboflavin, 5–500 mg magnesium and 250 mg–2 g potassium.

4. A nutritional composition suitable for the treatment of migraine, comprising in a daily dosage unit form 0.1–10 g taurine, 8–800 mg CoQ10 and 50–500 mg feverfew extract.

5. The nutritional composition according to claim 4, further comprising in said daily dosage unit form 0.5–20 g creatine.

6. The nutritional composition according to claim 4, further comprising in said daily dosage unit form 0.01–10 g L-carnitine or acylated carnitine.

7. The nutritional composition according to claim 4, further comprising in said daily dosage unit form 20 mg–2 g vitamin C.

8. The nutritional composition according to claim 4, further comprising in said daily dosage unit form 100–1500 IU of vitamin E.

9. The nutritional composition according to claim 4, further comprising in said daily dosage unit form 15–200 µg selenium.

10. The nutritional composition according to claim 4, further comprising in said daily dosage unit form one or more components selected from the group consisting of thiamine (1–100 mg), riboflavin (1–10 mg), magnesium (5–500 mg) and potassium (250 mg–2 g).

11. The nutritional composition according to claim 4, further comprising in said daily dosage unit form 5% to 125% of the average daily requirement of carbohydrates, proteins and fats.

12. A nutritional composition suitable for the treatment of migraine, comprising in a daily dosage unit form 0.1–10 g taurine, 8–800 mg CoQ10 and 50–500 mg ginger extract.

13. The nutritional composition according to claim 12, further comprising in said daily dosage unit form 0.5–20 g creatine.

14. The nutritional composition according to claim 12, further comprising in said daily dosage unit form 0.01–10 g L-carnitine or acylated carnitine.

15. The nutritional composition according to claim 12, further comprising in said daily dosage unit form 20 mg–2 g vitamin C.

16. The nutritional composition according to claim 12, further comprising in said daily dosage unit form 100–1500 IU of vitamin E.

17. The nutritional composition according to claim 12, further comprising in said daily dosage unit form 15–200 µg selenium.

18. The nutritional composition according to claim 12, further comprising in said daily dosage unit form one or more components selected from the groups consisting of thiamine (1–100 mg), riboflavin (1–10 mg), magnesium (5–500 mg) and potassium (250 mg–2 g).

19. The nutritional composition according to claim 12, further comprising in said daily dosage unit form 5% to 125% of the average daily requirement of carbohydrates, proteins and fats.

* * * * *